(12) United States Patent
Wu

(10) Patent No.: US 10,569,101 B2
(45) Date of Patent: Feb. 25, 2020

(54) PORTABLE IRRADIATION DEVICE AND METHOD FOR MANUFACTURING THE SAME

(71) Applicants: Boe Technology Group Co., Ltd., Beijing (CN); Boe Optical Science and Technology Co., Ltd., Jiangsu (CN)

(72) Inventor: Jiefei Wu, Beijing (CN)

(73) Assignees: BOE TECHNOLOGY GROUP CO., LTD., Beijing (CN); BOE OPTICAL SCIENCE AND TECHNOLOGY CO., LTD., Jiangsu (CN)

(*) Notice: Subject to any disclaimer, the term of this patent is extended or adjusted under 35 U.S.C. 154(b) by 487 days.

(21) Appl. No.: 15/325,802

(22) PCT Filed: Jul. 18, 2016

(86) PCT No.: PCT/CN2016/090262
§ 371 (c)(1),
(2) Date: Jan. 12, 2017

(87) PCT Pub. No.: WO2017/084367
PCT Pub. Date: May 26, 2017

(65) Prior Publication Data
US 2017/0304647 A1    Oct. 26, 2017

(30) Foreign Application Priority Data
Nov. 18, 2015  (CN) .......................... 2015 1 0793731

(51) Int. Cl.
*A61N 5/06*    (2006.01)

(52) U.S. Cl.
CPC ............. *A61N 5/0621* (2013.01); *A61N 5/06* (2013.01); *A61N 2005/0626* (2013.01); *A61N 2005/0649* (2013.01); *A61N 2005/0663* (2013.01)

(58) Field of Classification Search
CPC ....................................................... A61N 5/06
(Continued)

(56) References Cited

U.S. PATENT DOCUMENTS

2005/0251117 A1    11/2005  Anderson et al.
2008/0221504 A1*    9/2008  Aghion ................ A61H 7/008
                                                    604/20
(Continued)

FOREIGN PATENT DOCUMENTS

CN       1246379      3/2000
CN     201279301      7/2009
(Continued)

OTHER PUBLICATIONS

Second Office Action for Chinese Patent Application No. 201510793731.0 dated Nov. 15, 2017.
(Continued)

*Primary Examiner* — Lynsey C Eiseman
(74) *Attorney, Agent, or Firm* — Calfee, Halter & Griswold LLP

(57) ABSTRACT

A portable irradiation device is disclosed including: a hollow squeezing part operable to squeeze air therein out; a sucker having a first end opening portion and a second end opening portion, the first end opening portion being hermetically connected with the squeezing part, the second end opening portion being attachable to a human body by means of a difference in air pressure between inside and outside the sucker; and a blue light irradiation unit located in a space surrounded by the squeezing part, the sucker, or the squeezing part and the sucker. Also disclosed is a method for manufacturing a portable irradiation device.

18 Claims, 7 Drawing Sheets

(58) Field of Classification Search
USPC .................................................. 607/88–94
See application file for complete search history.

(56) References Cited

U.S. PATENT DOCUMENTS

| 2009/0018622 | A1 | 1/2009 | Asvadi et al. |
| 2009/0254155 | A1* | 10/2009 | Kanarsky ............. A61N 5/0613 607/89 |
| 2010/0049177 | A1* | 2/2010 | Boone, III ........... A61H 9/0057 606/9 |

FOREIGN PATENT DOCUMENTS

| CN | 101785744 | | 7/2010 |
| CN | 101785744 | A | 7/2010 |
| CN | 102327672 | | 1/2012 |
| CN | 102648989 | | 8/2012 |
| CN | 102962833 | A | 3/2013 |
| CN | 203075479 | | 7/2013 |
| CN | 103357122 | | 10/2013 |
| CN | 203263631 | A | 11/2013 |
| CN | 203915789 | | 11/2014 |
| CN | 204582318 | U | 8/2015 |
| CN | 105233421 | | 1/2016 |
| CN | 205163933 | | 4/2016 |
| CN | 205163933 | U | 4/2016 |
| KR | 20080094718 | | 10/2008 |
| KR | 101486642 | A | 10/2014 |

OTHER PUBLICATIONS

Search Report from European Application No. 16822361.8 dated Mar. 20, 2019.
First Office Action for Chinese Patent Application No. 201510793731.0 dated Apr. 12, 2017.
International Search Report and Written Opinion from PCT/CN16/90262 dated Oct. 13, 2016.

* cited by examiner

PORTABLE IRRADIATION DEVICE AND METHOD FOR MANUFACTURING THE SAME

REFERENCE TO THE RELATED APPLICATIONS

The present application is the U.S. national phase entry of PCT/CN2016/090262, with an international filing date of Jul. 18, 2016, which claims the benefit of Chinese Patent Application No. 201510793731.0 filed Nov. 18, 2015, the entire disclosures of which are incorporated herein by reference.

TECHNICAL FIELD

This disclosure relates to an irradiation device, and particularly to a portable irradiation device for treatment of neonatal jaundice and a method for manufacturing the same.

BACKGROUND

The current treatment of neonatal jaundice mainly comprises medical therapy and physical therapy, for example sunlight or blue light irradiation. A blue light therapeutic device is generally bulky and unsuitable for domestic use. Moreover, a newborn baby must wear an eye shield to avoid injuries to its eyes by the blue light. In order to prevent the newborn baby from getting rid of the eye shield, it is necessary to fix its body, which is very inhumane. Besides, the blue light may still escape out of the blue light therapeutic device during use and cause damage to eyes of the health care personnel.

Another therapeutic apparatus that is commonly used is blue light therapeutic clothes. However, it is inconvenient to put on the blue light therapeutic clothes, and the clothes may not fit well due to individual variations in bodies of newborn babies. Where the blue light therapeutic clothes do not fit, the blue light may escape and cause damage to eyes of the newborn baby and the health care personnel.

Therefore, an improved blue light irradiation apparatus is needed.

SUMMARY

In view of this, the present disclosure provides a portable irradiation device capable of alleviating or solving at least one of the above problems.

According to a first aspect of this disclosure, a portable irradiation device is provided, comprising: a hollow squeezing part operable to squeeze air therein out; a sucker having a first end opening portion and a second end opening portion, the first end opening portion being hermetically connected with the squeezing part, the second end opening portion being attachable to a human body by means of a difference in air pressure between inside and outside the sucker; and a blue light irradiation unit located in a space surrounded by the squeezing part, the sucker, or the squeezing part and the sucker.

In some embodiments, the squeezing part and the sucker are made of an elastic material.

In some embodiments, the elastic material comprises at least one of silica gel, rubber and elastic plastic.

In some embodiments, the portable irradiation device further comprises a control unit configured to ignite the blue light irradiation unit in response to the air pressure inside the sucker being smaller than or equal to a predetermined threshold, and to extinguish the blue light irradiation unit in response to the air pressure inside the sucker being greater than the predetermined threshold.

In some embodiments, the control unit comprises: an air pressure sensor for detecting the air pressure inside the sucker; and a controller configured to ignite or extinguishing the blue light irradiation unit in response to the air pressure detected by the air pressure sensor.

In some embodiments, the portable irradiation device further comprises an integrated circuit board on which the air pressure sensor, the controller and the blue light irradiation unit are integrated.

In some embodiments, the portable irradiation device further comprises a fixation frame encompassed in the space surrounded by the squeezing part, the sucker, or the squeezing part and the sucker for fixing a battery and the integrated circuit board. The battery is used for providing electric power for the air pressure sensor, the controller and the blue light irradiation unit.

In some embodiments, the blue light irradiation unit comprises one or more LED light emitting elements.

In some embodiments, the one or more LED light emitting elements are configured to emit blue light with a wavelength ranging from 400 nm to 490 nm.

In some embodiments, the one or more LED light emitting elements are arranged at an edge position of the integrated circuit board.

In some embodiments, the air pressure sensor and the controller are arranged at a central position of the integrated circuit board, and the one or more LED light emitting elements are arranged surrounding the air pressure sensor and the controller.

In some embodiments, the portable irradiation device further comprises an annular lens fixed on the second end opening portion for transmitting light emitted by the one or more LED light emitting elements.

In some embodiments, the one or more LED light emitting elements are arranged at a central position of the integrated circuit board.

In some embodiments, the squeezing part and the sucker are formed integrally.

In some embodiments, at least portion of the squeezing part is semi-transmissive such that it is illuminated by light emitted from the blue light irradiation unit when the blue light irradiation unit is ignited.

In some embodiments, the portable irradiation device is used for treatment of neonatal jaundice.

According to a second aspect of the present disclosure, a method for manufacturing a portable irradiation device is provided, comprising: providing an integrated circuit board on which an air pressure sensor, a controller and a blue light irradiation unit are integrated; fixing the integrated circuit board onto a fixation frame; providing a hollow squeezing part operable to squeeze air therein out; providing a sucker having a first end opening portion and a second end opening portion, the first end opening portion being hermetically connected with the squeezing part, the second end opening portion being attachable to a human body by means of a difference in air pressure between inside and outside the sucker; and mounting the fixation frame in a space surrounded by the squeezing part, the sucker, or the squeezing part and the sucker.

These and other aspects of the present invention will be apparent from and elucidated with reference to the embodiment(s) described hereinafter.

DETAILED DESCRIPTION

Figure 1:
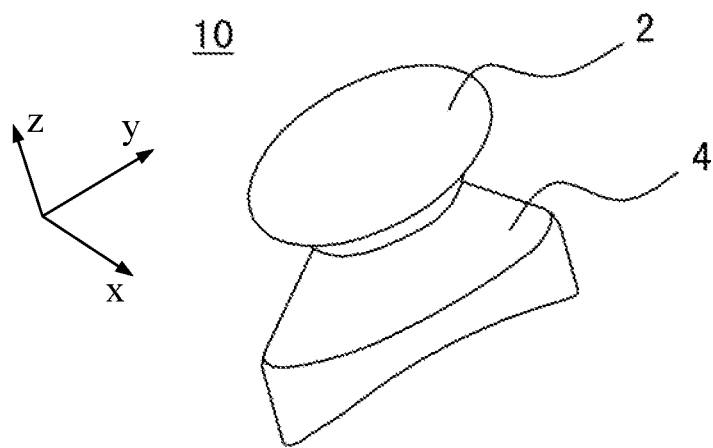
FIG. 1 schematically shows an outline view of a portable irradiation device according to an embodiment of this disclosure.

Embodiments of this disclosure will be described in detail with reference to the drawings. It will be understood that the drawings are not necessarily drawn to scale, but only for illustrative purposes.

Directional terms such as "above" and "below" are used hereinafter with reference to directions shown in the drawings, instead of in a restrictive sense.

FIG. 1 schematically shows an outline view of a portable irradiation device 10 according to an embodiment of this disclosure, wherein z-axis indicates a height direction of the portable irradiation device 10.

The portable irradiation device 10 comprises a squeezing part 2 for squeezing air therein out and a sucker 4 in gaseous communication with the squeezing part 2. The squeezing part 2 is hollow, and when it is squeezed, the air is squeezed out such that the portable irradiation device 10 can be attached to a human body of a newborn baby (not shown) for example by means of a difference in air pressure between inside and outside the sucker 4.

Figure 2A:
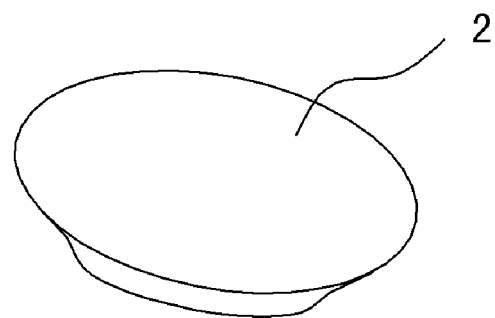
FIG. 2A schematically shows an outline view of a squeezing part of the portable irradiation device of FIG. 1 when viewed from above.
Figure 2B:
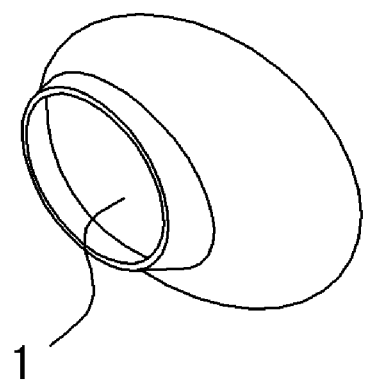
FIG. 2B schematically shows an outline view of a squeezing part of the portable irradiation device of FIG. 1 when viewed from below.

FIG. 2A schematically shows an outline view of the squeezing part 2 of the portable irradiation device 10 of FIG. 1 when viewed from above, and FIG. 2B schematically shows an outline view of the squeezing part 2 of the portable irradiation device 10 of FIG. 1 when viewed from below. With reference to FIG. 2B, the squeezing part 2 comprises an end opening 1.

Figure 3A:
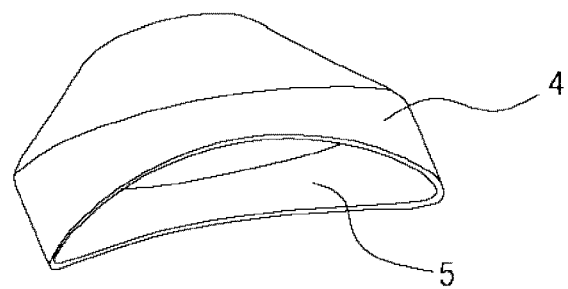
FIG. 3A schematically shows an outline view of a sucker of the portable irradiation device of FIG. 1 when viewed from below.
Figure 3B:
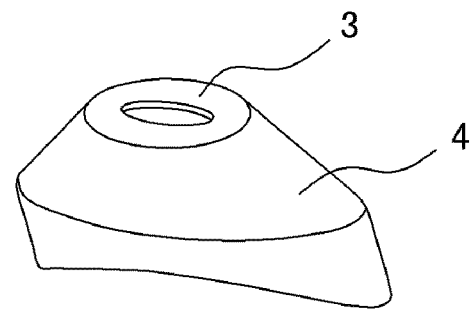
FIG. 3B schematically shows an outline view of a sucker of the portable irradiation device of FIG. 1 when viewed from above.

FIG. 3A schematically shows an outline view of the sucker 4 of the portable irradiation device 10 of FIG. 1 when viewed from below, and FIG. 3B schematically shows an outline view of the sucker 4 of the portable irradiation device 10 of FIG. 1 when viewed from above.

With reference to FIGS. 3A and 3B, the sucker 4 has a first end opening portion 3 which is hermetically connected with the squeezing part 2 via the end opening 1 of the squeezing part 2. The sucker 4 further has a second end opening portion 5 which is attachable to a human body of a newborn baby by means of a difference in air pressure between inside and outside the sucker 4 caused by a squeeze of the squeezing part 2.

The hermetical connection between the squeezing part 2 and the sucker 4 allows a certain degree of vacuum in the space surrounded by the squeezing part 2 and the sucker 4 such that the portable irradiation device 10 can be attached to the human body. In some embodiments, the hermetical connection can be implemented for instance by gluing. In some embodiments, the squeezing part 2 and the sucker 4 can be formed integrally. For example, the squeezing part 2 and the sucker 4 can be made of at least one elastic material selected from silica gel, rubber and elastic plastic by way of molding.

Since the space surrounded by the squeezing part 2 and the space surrounded by the sucker 4 are in communication, when the portable irradiation device 10 is attached to the human body via the second opening portion 5 of the sucker 4, the space surrounded by the squeezing part 2 and the space surrounded by the sucker 4 can be considered as having the same air pressure. Thus, "air pressure inside the sucker", "air pressure of the space surrounded by the sucker" and similar expressions should be understood to refer not only to the air pressure of the space surrounded by the sucker 4, but also to the air pressure of the space surrounded by the squeezing part 2.

Figure 4A:
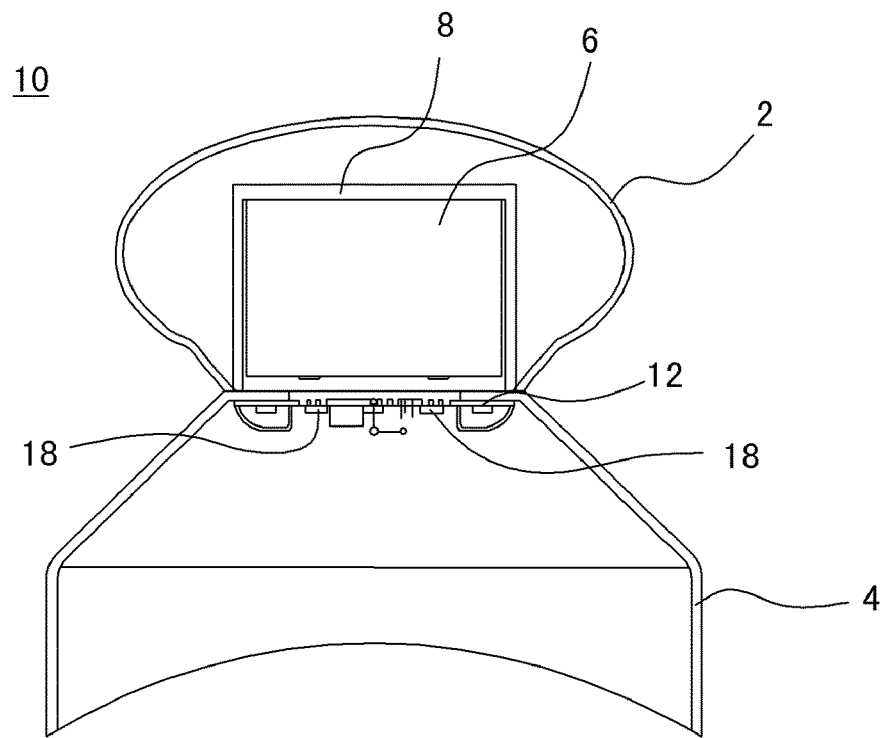
FIG. 4A schematically shows a cross-sectional view of the portable irradiation device of FIG. 1.
Figure 4B:
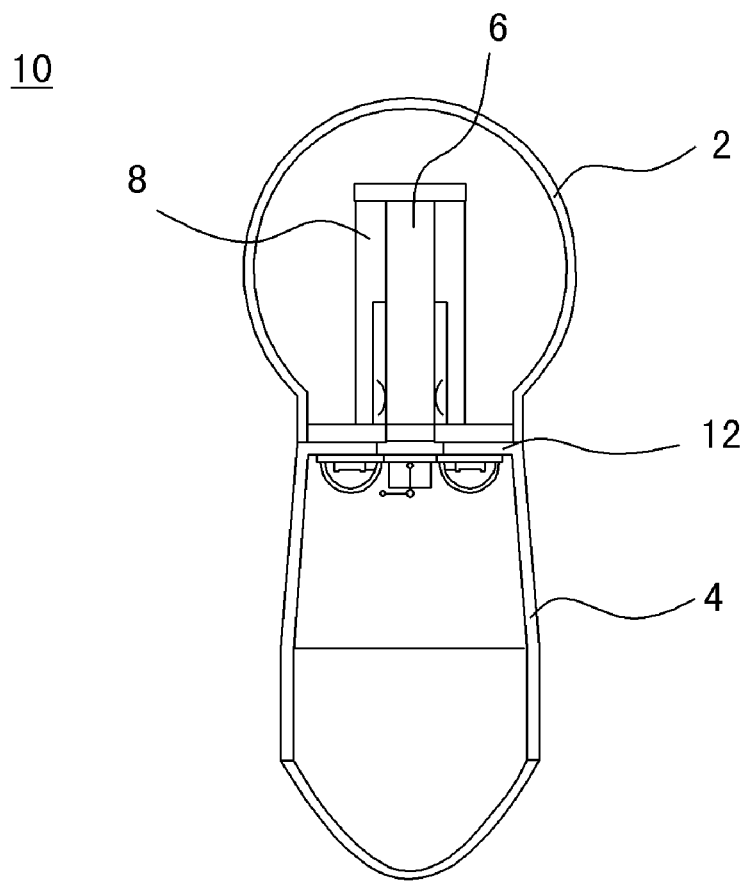
FIG. 4B schematically shows another cross-sectional view of the portable irradiation device of FIG. 1.

FIG. 4A schematically shows a cross-sectional view of the portable irradiation device 10 taken along y-axis as shown in FIG. 1, and FIG. 4B schematically shows a cross-sectional view of the portable irradiation device 10 taken along x-axis as shown in FIG. 1.

With reference to FIGS. 4A and 4B, the portable irradiation device 10 further comprises a blue light irradiation unit 18 located in the space surrounded by the squeezing part 2 and/or the sucker 4. FIG. 4A shows two irradiation units 18, which can be collectively referred to as the blue light irradiation unit 18. In the embodiment of FIG. 4A, the blue light irradiation unit 18 is disposed in the space surrounded by the sucker 4. Alternatively, the blue light irradiation unit 18 can be disposed in the space surrounded by the sucker 4. In other embodiments, part of the blue light irradiation unit 18 can be disposed in the space surrounded by the squeezing part 2, and the other part thereof can be disposed in the space surrounded by the sucker 4.

The portable irradiation device 10 may further comprise an integrated circuit board 12, a fixation frame 8 and a battery 6. As depicted below, the integrated circuit board 12 is fixed onto the fixation frame 8, and the fixation frame 8 can accommodate the battery 6.

Figure 5:
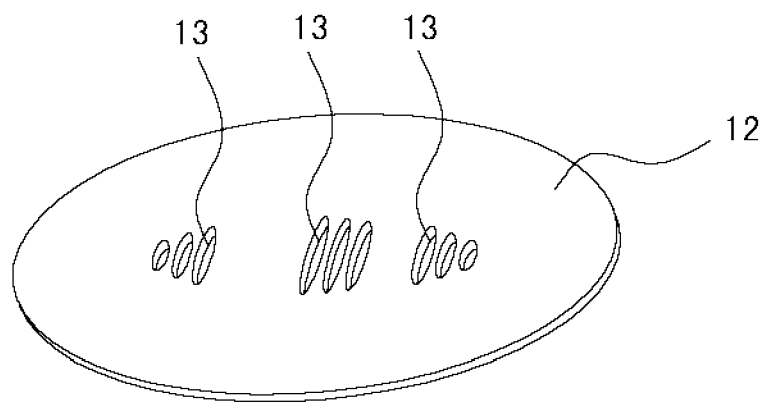
FIG. 5 schematically shows a schematic view of an integrated circuit board of a portable irradiation device according to an embodiment of this disclosure.

FIG. 5 schematically shows a schematic view of the integrated circuit board 12 of a portable irradiation device according to an embodiment of this disclosure. A plurality of grooves 13 are reserved in the integrated circuit board 12 for mounting electronic elements. The grooves 13 can further facilitate the gaseous communication between the squeezing part 2 and the sucker 4.

Figure 6:
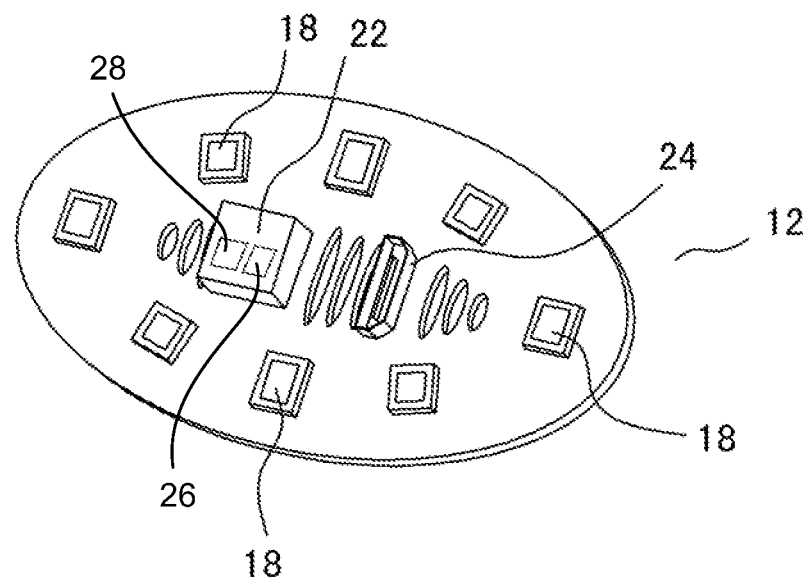
FIG. 6 schematically shows an outline view of an integrated circuit board of a portable irradiation device according to an embodiment of this disclosure, on which various elements are integrated.

FIG. 6 schematically shows an outline view of the integrated circuit board 12 of a portable irradiation device according to an embodiment of this disclosure, on which various elements are integrated.

With reference to FIG. 6, the blue light irradiation unit 18, a control unit 22 and a power line connection port 24 are integrated on the integrated circuit board 12. In embodiments, the integrated circuit board 12 is selected to adapt to elements of various package types, for example a surface mounting type or a dual in-line package (DIP) type.

The blue light irradiation unit 18 comprises one or more LED light emitting elements that can be configured to emit blue light with a wavelength ranging from 400 nm to 490 nm. The blue light with such a wavelength is effective in treating neonatal jaundice. After blue light irradiation, bilirubin in the blood of a newborn baby will rapidly decrease. Therefore, the above portable irradiation device can be used for treatment of neonatal jaundice.

Figure 7:
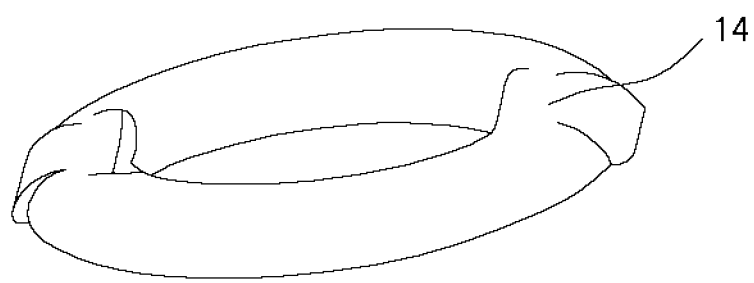
FIG. 7 schematically shows an outline view of an annular lens of a portable irradiation device according to an embodiment of this disclosure.

In the embodiment of FIG. 6, the blue light irradiation unit 18 comprises a plurality of LED light emitting elements arranged at an edge position of the integrated circuit board 12. Specifically, the plurality of LED light emitting elements are arranged surrounding the control unit 22 and the power line connection port 24 on the integrated circuit board 12. In certain embodiments, the portable irradiation device 10 may comprise an annular lens 14 for transmitting light emitted by the blue light irradiation unit 18 as shown in FIG. 7. In addition to guiding the light transmitted by the LED light emitting elements distributed in the edge position of the integrated circuit board 12, the annular lens 14 can be further used for protecting the LED light emitting elements against static electricity and moisture. The annular lens 14 may be fixed on the second end opening portion 5 of the sucker 4.

In other embodiments, the blue light irradiation unit 18 may comprise a plurality of LED light emitting elements arranged at a central position of the integrated circuit board 12. In either case, the plurality of LED light emitting elements may be evenly distributed on the integrated circuit board 12 to provide uniform blue light irradiation.

The control unit 22 is configured to ignite the blue light irradiation unit 18 in response to the air pressure inside the sucker 4 being smaller than or equal to a predetermined threshold, and to extinguish the blue light irradiation unit 18 in response to the air pressure inside the sucker 4 being greater than the predetermined threshold. In the embodiment of FIG. 6, the control unit 22 comprises an air pressure sensor 26 and a controller 28. The air pressure sensor 26 detects the air pressure inside the sucker 4, and the controller 28 ignites or extinguishes the blue light irradiation unit 18 based on the air pressure detected by the air pressure sensor 26. Although the air pressure sensor 26 and the controller 28 in FIG. 6 are shown as being integrated in the control unit 22, they may also be arranged separately.

Figure 8:
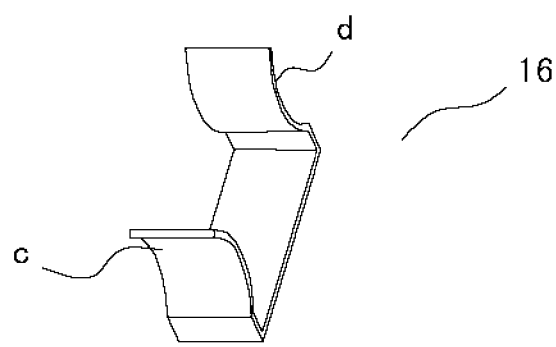
FIG. 8 schematically shows an outline view of a spring sheet of a portable irradiation device according to an embodiment of this disclosure.
Figure 9:
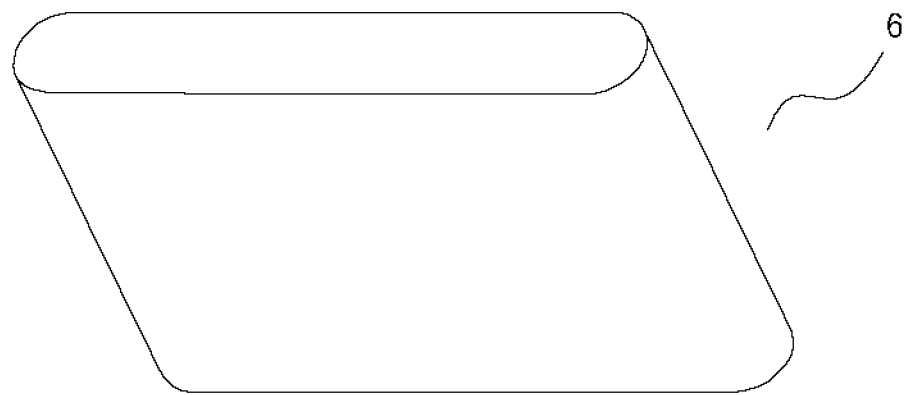
FIG. 9 schematically shows an outline view of a battery of a portable irradiation device according to an embodiment of this disclosure.

The power line connection port 24 provides connection to a power source for the integrated circuit board 12. A spring sheet 16 as shown in FIG. 8 is fixed on the power line connection port 24, and has elastic ends c and d. The battery 6 as shown in FIG. 9 is clamped between the elastic ends c and d of the spring sheet 16 and configured for providing electric power via the elastic ends c and d to elements on the integrated circuit board 12, for example, to the control unit 22 and the blue light irradiation unit 18 on the integrated circuit board 12. In an embodiment where the battery 6 is a rechargeable battery, the battery 6 can be recharged via the elastic ends c and d of the spring sheet 16.

Figure 10:
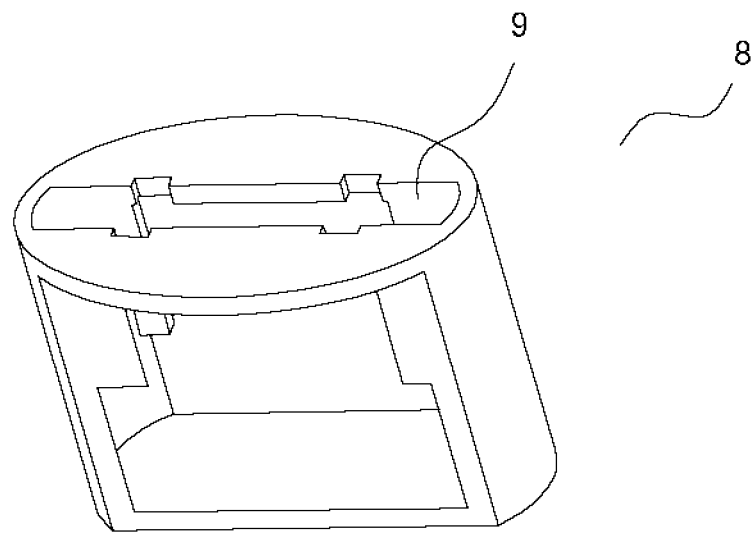
FIG. 10 schematically shows an outline view of a fixation frame of a portable irradiation device according to an embodiment of this disclosure.

FIG. 10 schematically shows an outline view of the fixation frame 8 of a portable irradiation device according to an embodiment of this disclosure.

The fixation frame 8 comprises a slot 9 for inserting the battery 6 as shown in FIG. 8. Besides, the integrated circuit board 12 may be fixed onto the bottom of the fixation frame 8. In this case, the blue light irradiation unit 18 integrated on the integrated circuit board 12 is advantageously arranged to emit blue light towards the second end opening portion 5 of the sucker 4.

The fixation frame 8 is encompassed in a space surrounded by the squeezing part 2 and/or the sucker 4. In some embodiments, the fixation frame 8 may be completely encompassed in the space surrounded by the squeezing part 2 as shown in FIGS. 2A and 2B. In some embodiments, the fixation frame 8 can be completely encompassed in the space surrounded by the sucker 4 (not shown). In some embodiments, part of the fixation frame 8 is located in the space surrounded by the squeezing part 2 and the other part thereof is located in the space surrounded by the sucker 4 (not shown). It will be understood that the fixation frame 8 can be specifically arranged upon needs.

Figure 11:
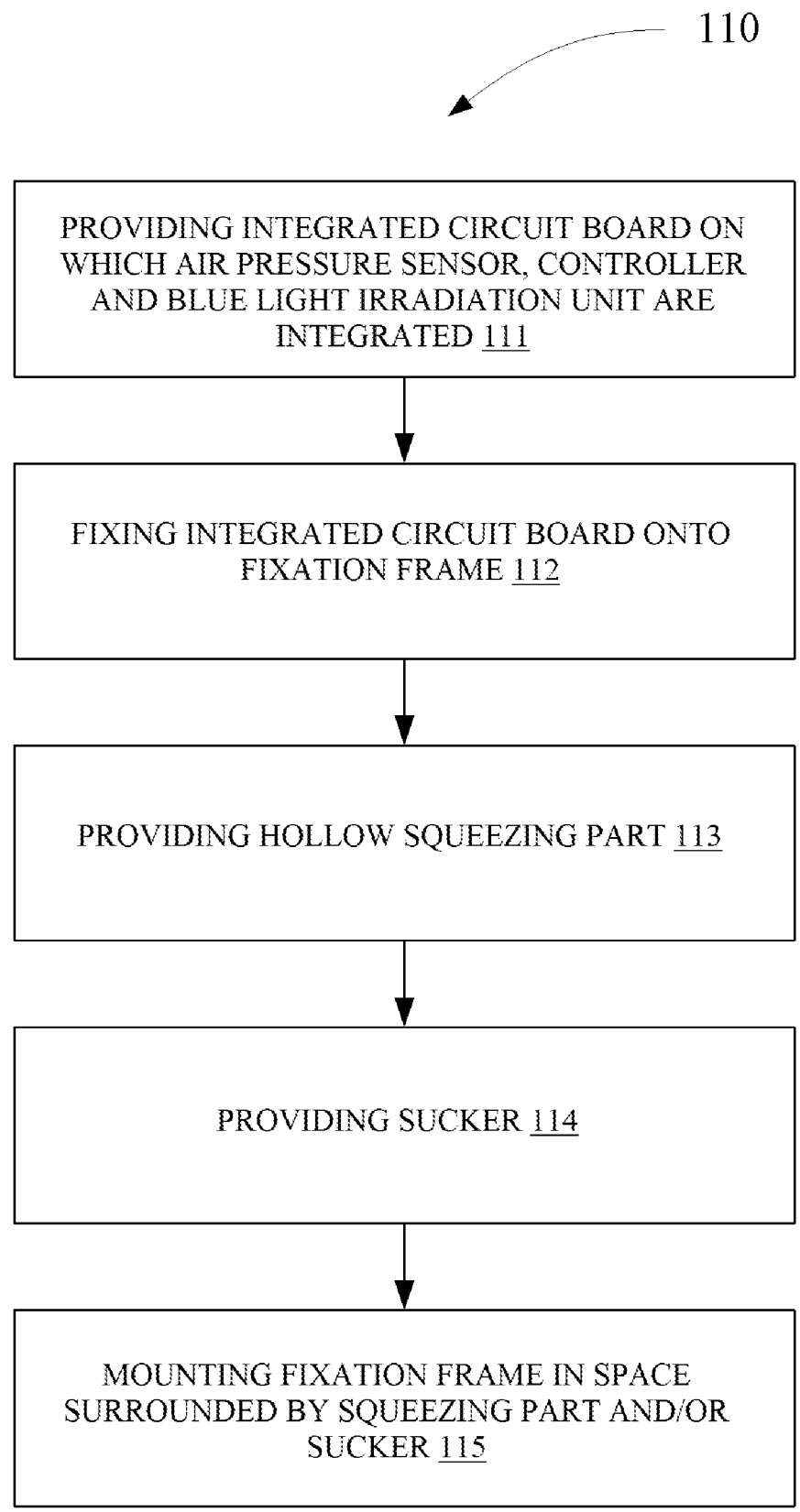
FIG. 11 is a flow diagram of a method for manufacturing a portable irradiation device according to an embodiment of this disclosure.

FIG. 11 is a flow diagram of a method 110 for manufacturing a portable irradiation device according to an embodiment of this disclosure. The method 110 comprises steps as follows.

In step 111, an integrated circuit board on which an air pressure sensor, a controller and a blue light irradiation unit are integrated is provided.

In step 112, the integrated circuit board is fixed onto a fixation frame. Specifically, the integrated circuit board can be fixed onto the bottom of the fixation frame for example by screw locking, riveting or welding.

In step 113, a hollow squeezing part operable to squeeze air therein out is provided.

In step 114, a sucker having a first end opening portion and a second end opening portion is provided, wherein the first end opening portion is hermetically connected with the squeezing part, and the second end opening portion is attachable to a human body by means of a difference in air pressure between inside and outside the sucker. In some embodiments, the hermetic connection can be implemented for example by gluing.

In step 115, the fixation frame is mounted in a space surrounded by the squeezing part and/or the sucker.

In an embodiment where the portable irradiation device comprises an annular lens, the annular lens may be further fixed on the second end opening portion of the sucker.

Figure 12:
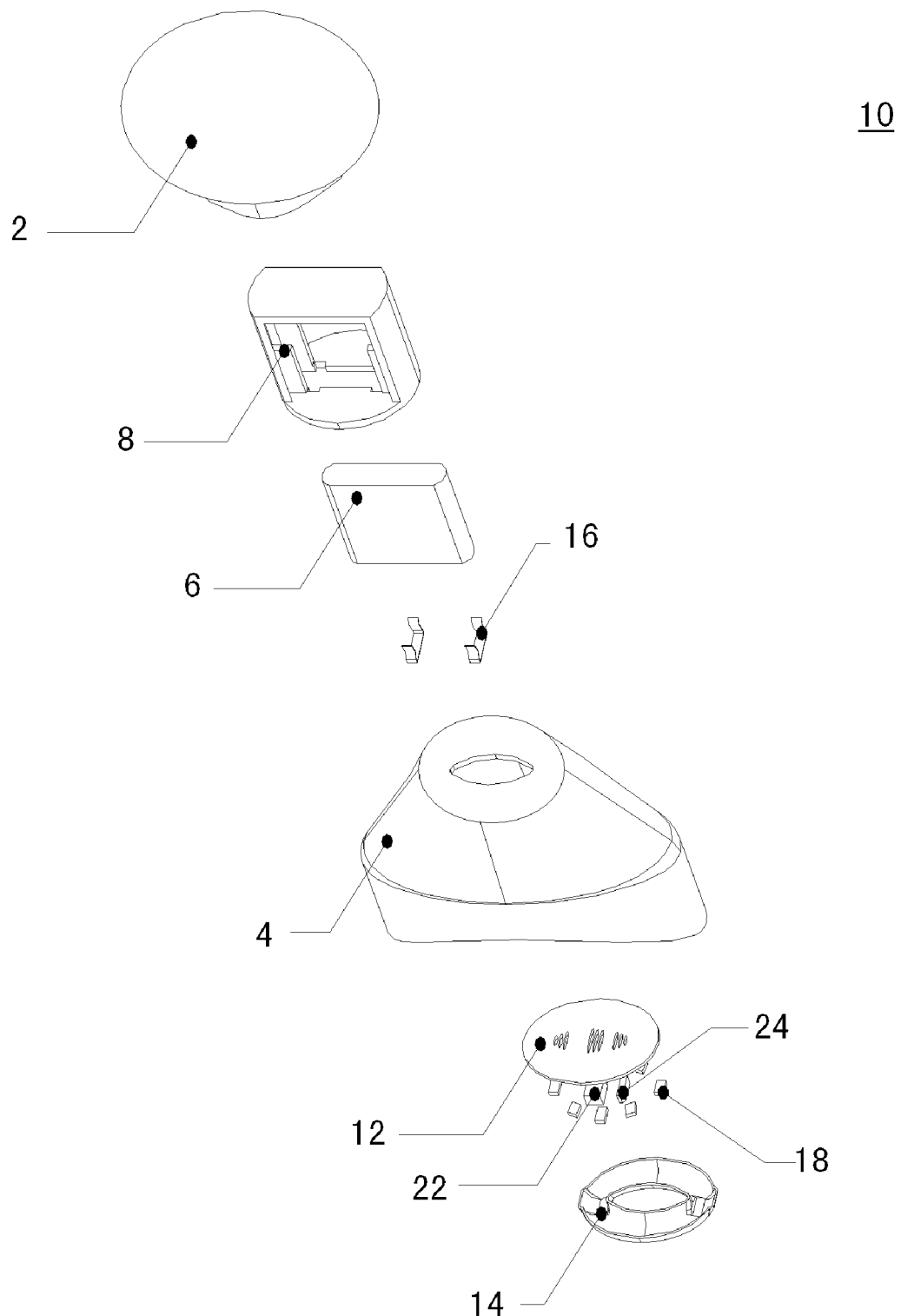
FIG. 12 schematically shows an assembling view of a portable irradiation device according to an embodiment of this disclosure.

FIG. 12 schematically shows an assembling view of the portable irradiation device 10 according to an embodiment of this disclosure.

The portable irradiation device 10 comprises a squeezing part 2, a fixation frame 8, a battery 6, a spring sheet 16, a sucker 4 and an integrated circuit board 12 on which a control unit 22, blue light irradiation unit 18 and a power line connection port 24 are integrated. In certain embodiments, the portable irradiation device 10 may comprise an annular lens 14.

As mentioned above, the fixation frame 8 (including related components fixed on the fixation frame 8, such as the battery 6, the spring sheet 16 and the integrated circuit board 12) can be encompassed in a space surrounded by the squeezing part 2, or in a space surrounded by the sucker 4. Alternatively, part of the fixation frame 8 is located in the space surrounded by the squeezing part 2 and the other part thereof is located in the space surrounded by the sucker 4. In other words, the fixation frame 8 can be specifically arranged upon needs.

In the embodiment as shown in FIG. 12, the fixation frame 8, the battery 6 and the spring sheet 16 will be all assembled in the space surrounded by the squeezing part 2, and the integrated circuit board 12 and the annular lens 14 will be assembled in the space surrounded by the sucker 4.

During the use of the portable irradiation device 10, the second end opening portion 5 of the sucker 4 is placed on a human body for example a newborn baby, and the squeezing part 2 is squeezed such that (a portion of) the air surrounded by the squeezing part 2 is squeezed out. By means of a difference in air pressure between inside and outside the sucker 4 due to the squeeze of the squeezing part 2, the sucker 4 is attached to a human body for example a newborn baby. Then, the air pressure sensor 26 detects the air pressure inside the sucker 4, and the controller 28 ignites or extinguishes the blue light irradiation unit 18 based on the air pressure detected by the air pressure sensor 26. For example, when the air pressure inside the sucker 4 is smaller than or equal to a predetermined threshold, the blue light irradiation unit 18 is ignited; when the air pressure inside the sucker 4 is greater than the predetermined threshold, the blue light irradiation unit 18 is extinguished. The predetermined threshold can be preset, for example as 0.4, 0.5, 0.6, 0.7, 0.8, 0.9 or 0.92 atm. When the air pressure inside the sucker 4 is smaller than or equal to the predetermined threshold, the sucker 4 can be firmly attached to a human body for example a newborn baby. At this point, the blue light irradiation unit 18 is ignited and no blue light will escape out of the portable irradiation device 10. When the air pressure inside the sucker 4 is greater than the predetermined threshold, the sucker 4 will no longer be firmly attached to the human body. At this point, the blue light irradiation unit 18 is extinguished to prevent the blue light from escaping out of the portable irradiation device 10. The lower the predetermined threshold is, the higher the security coefficient will be, i.e., the less likely the blue light is to escape out of the portable irradiation device 10. For example, it is safer to set the predetermined threshold as 0.9 atm than as 0.92 atm.

In some embodiments, at least portion of the squeezing part 2 is semi-transmissive. When the blue light irradiation unit 18 is ignited, the squeezing part 2 is illuminated by light emitted from the blue light irradiation unit 18. When the blue light irradiation unit 18 is extinguished, the squeezing part 2 will not be illuminated. Thus the state of the squeezing part 2 can indicate whether the portable irradiation device 10 is in use.

As compared with a prior art blue light therapeutic device, the portable irradiation device of this disclosure is more convenient in use. In particular, it is unnecessary to cover the eyes of a newborn baby with an eye shield. As compared with blue light therapeutic clothes for neonatal jaundice in the prior art, the portable irradiation device of this disclosure avoids complicated operations involved in putting on the therapeutic clothes.

Although this disclosure has been described with reference to the above embodiments, it should be understood that this disclosure is not limited to the embodiments disclosed. Rather, this disclosure is intended to cover all modifications and variations that fall within the spirit and scope of the appending claims.

The invention claimed is:

1. A portable irradiation device, comprising:
a hollow squeezing part operable to squeeze air therein out;
a sucker having a first end opening portion and a second end opening portion, the first end opening portion being hermetically connected with the squeezing part, the second end opening portion being attachable to a human body by means of a difference in air pressure between inside and outside the sucker;
a blue light irradiation unit located in a space surrounded by the squeezing part, the sucker, or the squeezing part and the sucker;
an integrated circuit board on which the blue light irradiation unit, an air pressure sensor, and a controller are integrated, wherein the integrated circuit board is arranged at the first end opening portion and is provided with a plurality of grooves to provide gaseous communication between the squeezing part and the sucker; and
a fixation frame encompassed in the space surrounded by the squeezing part, the sucker, or the squeezing part and the sucker for fixing a battery and the integrated circuit board, wherein the fixation frame and the integrated circuit board are mounted perpendicular to each other.

2. The portable irradiation device according to claim 1, wherein the squeezing part and the sucker are made of an elastic material.

3. The portable irradiation device according to claim 2, wherein the elastic material comprises at least one of silica gel, rubber and elastic plastic.

4. The portable irradiation device according to claim 3, wherein the air pressure sensor is configured to detect air pressure inside the sucker, and wherein the controller is configured to ignite the blue light irradiation unit in response to the air pressure inside the sucker being smaller than or equal to a predetermined threshold, and to extinguish the blue light irradiation unit in response to the air pressure inside the sucker being greater than the predetermined threshold.

5. The portable irradiation device according to claim 1, wherein the battery is used for providing electric power for the air pressure sensor, the controller and the blue light irradiation unit.

6. The portable irradiation device according to claim 5, wherein the blue light irradiation unit comprises one or more LED light emitting elements.

7. The portable irradiation device according to claim 6, wherein the one or more LED light emitting elements are configured to emit blue light with a wavelength ranging from 400 nm to 490 nm.

8. The portable irradiation device according to claim 6, wherein the one or more LED light emitting elements are arranged at an edge position of the integrated circuit board.

9. The portable irradiation device according to claim 8, wherein the air pressure sensor and the controller are arranged at a central position of the integrated circuit board, and wherein the one or more LED light emitting elements are arranged surrounding the air pressure sensor and the controller.

10. The portable irradiation device according to claim 8, further comprising an annular lens fixed on the second end opening portion for transmitting light emitted by the one or more LED light emitting elements.

11. The portable irradiation device according to claim 6, wherein the one or more LED light emitting elements are arranged at a central position of the integrated circuit board.

12. The portable irradiation device according to claim 1, wherein the squeezing part and the sucker are formed integrally.

13. The portable irradiation device according to claim 4, wherein at least portion of the squeezing part is semi-transmissive such that it is illuminated by light emitted from the blue light irradiation unit when the blue light irradiation unit is ignited.

14. The portable irradiation device according to claim 1, wherein the portable irradiation device is used for treatment of neonatal jaundice.

15. A method for manufacturing a portable irradiation device, wherein the portable irradiation device comprises: a hollow squeezing part operable to squeeze air therein out a sucker having a first end opening portion and a second end opening portion, the first end opening portion being hermetically connected with the squeezing part, the second end opening portion being attachable to a human body by means of a difference in air pressure between inside and outside the sucker; a blue light irradiation unit located in a space surrounded by the squeezing part, the sucker, or the squeezing part and the sucker; an integrated circuit board on which the blue light irradiation unit, an air pressure sensor, and a controller are integrated, wherein the integrated circuit board is arranged at the first end opening portion and is provided with a plurality of grooves to provide gaseous communication between the squeezing part and the sucker; and a fixation frame encompassed in the space surrounded by the squeezing part, the sucker, or the squeezing part and the sucker for fixing a battery and the integrated circuit board, wherein the fixation frame and the integrated circuit board are mounted perpendicular to each other,
the method comprising:
providing the integrated circuit board;
fixing the integrated circuit board onto the fixation frame, wherein the fixation frame and the integrated circuit board are perpendicular to each other;
providing the hollow squeezing part;
providing the sucker; and
mounting the fixation frame in the space surrounded by the squeezing part, the sucker, or the squeezing part and the sucker.

16. The method according to claim 15, wherein the blue light irradiation unit comprises one or more LED light emitting elements.

17. The method according to claim 16, wherein the one or more LED light emitting elements are configured to emit blue light with a wavelength ranging from 400 nm to 490 nm.

18. The portable irradiation device according to claim 2, wherein the portable irradiation device is used for treatment of neonatal jaundice.

* * * * *